United States Patent
Braam et al.

(10) Patent No.: US 10,613,078 B2
(45) Date of Patent: Apr. 7, 2020

(54) ASSAYS FOR MEASURING CARDIOTOXICITY

(71) Applicant: NCARDIA B.V., Leiden (NL)

(72) Inventors: Stefan Robbert Braam, Leiden (NL); Fleur Stevenhagen, Leiden (NL)

(73) Assignee: NCARDIA B.V., Leiden (NL)

(*) Notice: Subject to any disclaimer, the term of this patent is extended or adjusted under 35 U.S.C. 154(b) by 33 days.

(21) Appl. No.: 15/552,333

(22) PCT Filed: Feb. 18, 2016

(86) PCT No.: PCT/NL2016/050118
§ 371 (c)(1),
(2) Date: Aug. 21, 2017

(87) PCT Pub. No.: WO2016/133392
PCT Pub. Date: Aug. 25, 2016

(65) Prior Publication Data
US 2018/0038846 A1   Feb. 8, 2018

(30) Foreign Application Priority Data

Feb. 20, 2015 (NL) .................................... 2014331

(51) Int. Cl.
*G01N 33/50* (2006.01)
*C12N 5/077* (2010.01)

(52) U.S. Cl.
CPC ....... *G01N 33/5014* (2013.01); *C12N 5/0657* (2013.01); *G01N 33/5061* (2013.01)

(58) Field of Classification Search
CPC ........... G01N 33/5014; G01N 33/5061; C12N 5/0657
USPC ........................................................ 435/29
See application file for complete search history.

(56) References Cited

U.S. PATENT DOCUMENTS

| 2011/0212461 A1 | 9/2011 | Bitter et al. |
| 2011/0312090 A1 | 12/2011 | Meyer et al. |
| 2013/0029368 A1 | 1/2013 | Kattman et al. |

FOREIGN PATENT DOCUMENTS

| WO | 2009146887 A2 | 12/2009 | |
| WO | 2014093051 A2 | 6/2014 | |
| WO | 2014200339 A1 | 12/2014 | |
| WO | WO 2015/025030 | * 2/2015 | ............. C12N 5/071 |

OTHER PUBLICATIONS

Tohyama et al., Distinct Metabolic Flow Enables Large-Scale Purification of Mouse and Human Pluripotent Stem Cell-Derived Cardiomyocytes, Cell Stem Cell, 12 (2013), p. 127-137.*
Eldridge Sandy et al.,"Examining the Protective Role of ErbB2 Modulation in Human-Induced Pluripotent Stem Cell-Derived Cardiomyocyte", Toxicological Science, pp. 547-559, vol. 141, No. 2 (Oct. 2014).
Braam et al.,"Cardiomyocytes from human pluripotent stem cells in regenerative medicine and drug discovery", Trends in Pharmacological Sciences, pp. 536-545, vol. 30, No. 10 (Oct. 2009).
Rana et al., Characterization of Human-Induced Pluripotent Stem Cell-Derived Cardiomyocytes: Bioenergetics and Utilization in Safety Screening, Toxicological Sciences, 130(1):117-131 (2012).

* cited by examiner

*Primary Examiner* — Jennifer M. H. Tichy
(74) *Attorney, Agent, or Firm* — Browdy and Neimark, PLLC

(57) ABSTRACT

The current disclosure relates to technology for predicting cardiotoxicity of compounds. In vitro methods using human stem-cell derived cardiomyocytes cultured in specific media are disclosed, as well as kits for use in the method. In the method, the cells are treated with a test compound in combination with a mitochondrial toxicant.

16 Claims, 5 Drawing Sheets

US 10,613,078 B2

ASSAYS FOR MEASURING CARDIOTOXICITY

FIELD OF THE INVENTION

The current disclosure relates to technology for predicting cardiotoxicity of compounds. In vitro methods using human stem-cell derived cardiomyocytes cultured in specific media are disclosed, as well as kits for use in the method. In the method, the cells are treated with a test compound in combination with a mitochondrial toxicant.

PRIOR ART

This disclosure generally relates to the field of toxicology. More particularly, the invention relates to methods for predicting cardiotoxicity, and methods for screening compounds for potential cardiotoxicity.

Cardiomyocytes are the contractile cells in the heart and have the ability to respond to various hormonal, neural, electrical and mechanical signals through a variety of receptors, channels and transporters present on the cell surface and in the cell and nucleus. Cardiomyocytes respond to many physiological agents as wells as to many non-physiological agents like pharmaceuticals and toxicants.

Because of the need to regulate contraction strength and heart rate both during health and disease, understanding the cardiotoxic potential of compounds, in particular potential drugs, is critical. This is for example, not only true for (potential) cardiovascular drugs but also for drugs or candidate drugs aimed at other conditions. Indeed the development of inhibitors and drugs has shown liabilities with regards to cardiotoxicity. One area where this is in particular the case is cancer therapy. For example, cardiotoxicity was reported for treatments involving trastuzumab, the antibody that targets the ERBB2 receptor. Adverse cardiac effects have also been reported for other compounds such as kinase inhibitors, cox-2 inhibitors, fibrates and anthracyclines. Examples of compounds with known cardiovascular toxicity include imatinib, cetuximab, dasatinib, doxorubicin and bevacizumab (see for example Schimmel et al. Cancer Treatment Reviews 2004; 30:181-191 (http://dx.doi.org/10.1016/j.ctrv.2003.07.003 or Force et al. Nature Reviews Drug Discovery 2011; 10, 111-126 doi:10.1038/nrd3252)).

In the art it is recognized that mitochondrial dysfunction is increasingly implicated in the etiology of such drug-induced (cardio) toxicities and that members of diverse drug classes undermine mitochondrial function, and among the most potent are drugs that have been withdrawn from the market, or have received Black Box warnings from the FDA (see Dykens et al (2007) Drug Discovery Today 12:17-18: 777-785).

It is often the case the cardiotoxic often remains undetected until large numbers of patients have been exposed to the drug and evidence indicates that mitochondrial dysfunction played a role in the toxicity that forced the withdrawal of several drugs including, for example, troglitazone and cerivastatin.

To avoid mitochondrial liabilities, routine screens need to be positioned within the drug-development process, preferably as soon as possible. Cardiotoxicity needs to be determined for each agent or compound on a case-by-case basis, requiring assays that a repeatable and that are predictive for the in vivo situation.

We have now invented a method helpful in predicting which compounds or therapy may demonstrate cardiotoxicity in in vivo toxicity studies by testing the compounds using a specific in vitro assay using human stem-cell derived cardiomyocytes that have been cultured under specific conditions.

DESCRIPTION

Definitions

Figure 1:
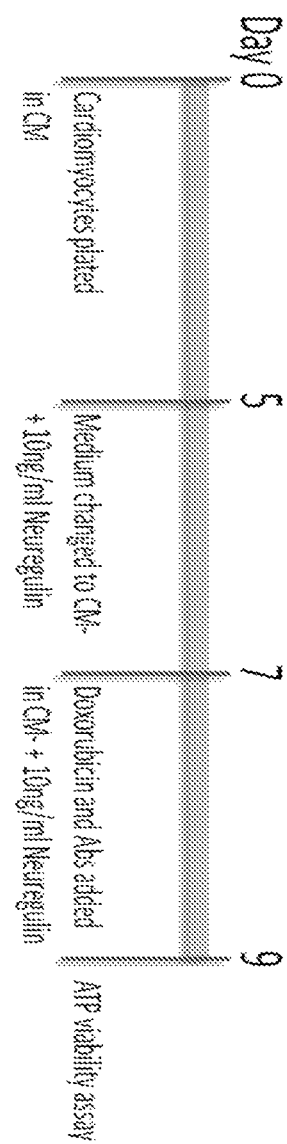
FIG. 1: Example of culturing scheme

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.//nlp It is contemplated that any method or composition described herein can be implemented with respect to any other method or composition described herein.

Embodiments discussed in the context of methods and/or compositions of the invention may be employed with respect to any other method or composition described herein. Thus, an embodiment pertaining to one method or composition may be applied to other methods and compositions of the invention as well.

As used herein "a" or "an" may mean one or more. When used in conjunction with the word "comprising", the words "a" or "an" may mean one or more than one.

As used herein "cardiomyocytes" refers to any cardiomyocyte lineage cells; the cells may be at any stage of cardiomyocyte ontogeny, unless otherwise specified. For example, cardiomyocytes may include both cardiomyocyte precursor cells and mature cardiomyocytes.

As used herein "stem cell" refers to cells that may be stably multiplied and cultured in vitro and that are totipotent, pluripotent, induced pluripotent, multipotent, oligopotent, or unipotent cells, preferably at least pluripotent. By that it is meant that the cells can differentiate into (many) different mature differentiated cell types of the (human or animal)

body. Embryonic stem cells are pluripotent stem cells derived from early embryos. Embryonic stem cells are pluripotent cells derived from the inner cell mass of a blastocyst. Methods for obtaining, maintaining and culturing embryonic cells are well-known to the skilled person, for example, as described by Chung et al. (Cell Stem Cell. 2008; (2):113-117). This method describes human embryonic stem cell generated without embryo destruction. The term includes embryonic stem cells obtained from cultures of ES cell lines.

The term "induced pluripotent stem cell", or iPSC, refers to a type of pluripotent stem cell that is artificially prepared from a non-pluripotent cell, for example from an adult somatic cell, or terminally differentiated cell, such as fibroblast, a hematopoietic cell, a myocyte, a neuron, an epidermal cell, or the like. The iPSCs are obtained by treating the non-pluripotent cell with reprogramming factors, for example by using methods known to the skilled person, for example as described by Takahashi et al. (Cell. 2007; 131(5):861-72). Such iPSCs can differentiate into cell types of the three germ layers in vitro and in teratomas. Induced pluripotent stem cells display the characteristics of embryonic stem cells.

The term "pluripotent stem cell" refers to a cell capable of being differentiated into cells of all three germinal layers (endoderm, mesoderm and ectoderm). Although in theory a pluripotent stem cell can differentiate into any cell of the body, the experimental determination of pluripotency is generally based on differentiation of a pluripotent cell into several cell types of each germinal layer. The pluripotent stem cell may for example be an embryonic stem or an induced pluripotent stem cell derived by reprogramming somatic cells.

The term "stem cell-derived cardiomyocytes" as used herein refers to cardiomyocytes that are generated from pluripotent stem cells, for examples from human pluripotent stem cells such as human embryonic stem cells or human induced pluripotent stem cells, by the process of differentiation. In particular, within the context of the current invention, the term "stem cell-derived cardiomyocytes" refers to such cardiomyocytes obtained by in vitro culturing, for example by in vitro differentiation of human pluripotent stem cells. Such stem cell-derived cardiomyocytes may be spontaneously contractile cells derived by in vitro methods from a human pluripotent cell, although sometimes non-contractile cells can be obtained. The cells still manifest other of the typical characteristics of cells that were in vitro differentiated into cardiomyocytes, and using differentiation protocols aimed at obtaining stem-cell derived cardiomyocytes and are in the art also referred to as (in vitro obtained) stem-cell derived cardiomyocytes. Recent reviews defining and describing stem-cell derived cardiomyocytes, have covered methods to create (e.g. Vidarsson et al. Stem Cell Rev. 2010; 6(1):108-120, Boheler et al. Circ Res. 2002; 91(3): 189-201. Mummery et al. Circ Res. 2012; 111(3):344-358, and Jiang et al. J Cell Mol Med. 2012; 16(8):1663-1668, David et al. Physiology (Bethesda) 2012; 27(3):119-129), and purify (Habib et al. J Mol Cell Cardiol. 2008; 45(4): 462-474) stem-cell derived cardiomyocytes, as well as their electrophysiology (Blazeski et al. Prog Biophys Mol Biol. 2012; 110(2):178-195).

It is understood that cardiomyocytes obtained from an adult or mature heart, e.g. human heart, are understood to not be "stem cell-derived cardiomyocytes" within the context of the current disclosure.

The term "cardiotoxic compound" as used herein refers to compounds that cause direct or indirect injury to cardiomyocytes and the myocardium that may manifest in certain clinical symptoms which may include: congestive heart failure, ischemia, hypotension, hypertension, arrhythmias (e.g. bradycardia), edema, QT prolongation and conduction disorders, and thromboembolism. Cardiotoxicity of a compound is generally recognized by the skilled person. Cardiotoxicity per se may for example be established by the person skilled in the art using methods such as measuring oxygen consumption rate (OCR), extracellular acidification rate (ECAR) ATP levels, mitochondrial membrane potential measurements, mitochondria biogenesis assays, OXPHOS enzyme assays and apoptosis/ necrosis markers.

Examples are described in US2011212461 and in Liza A. Pon, Eric A. Schon—2011—Methods in Cell Biology VOLUME 80 Mitochondria, 2nd Edition Edited by Liza A. Pon et al (ISBN-13: 978-0-12-544173-5).

Cardiotoxicity importantly also includes toxicity of a compound for the mitochondria of cardiomyocytes. In other words, if a compound, when tested in cardiomyocytes, display mitochondrial toxicity, such compound is considered a potential or true cardiotoxic compound and may thus manifest itself in clinical symptoms as described above. So, cardiotoxicity includes mitochondrial toxicity in cardiomyocytes, including mitochondrial toxicity in human stem-cell derived cardiomyocytes, including mitochondrial toxicity in human stem-cell derived cardiomyocytes cultured on a medium not comprising glucose and/or galactose but comprising carnitine and fatty acids. In other words, if a compound is determined as showing mitochondrial toxicity in (step c of) the method of the invention using stem cell derived cardiomyocytes, such compound is by definition considered a cardiotoxic compound.

As a non-limiting example, compounds display cardiotoxicity if they cause direct or indirect injury to cardiomyocytes comparable to that observed by any one of the various cardiotoxic compounds described herein.

The term "mitochondrial toxicant" as used herein refers to compounds that cause direct or indirect injury to mitochondria, in particular cardiomyocyte mitochondria, for example as determined in stem cell derived cardiomyocytes. Toxicity of a compound for mitochondria is generally recognized by the skilled person (see for example Meyer et al, ToxSci (2013), doi:10.1093/toxsci/kft102). Mitochondrial toxicity of a compound may for example be established by the person skilled in the art using methods such as those described in in US2011212461 and in Liza A. Pon, Eric A. Schon—2011 —Methods in Cell Biology VOLUME 80 Mitochondria, 2nd Edition Edited by Liza A. Pon et al (ISBN-13: 978-0-12-544173-5). Mitochondrial toxicity is often directly linked to and may cause cardiotoxicity. In other words, a mitochondrial toxicant may cause direct or indirect injury to cardiomyocytes, as described herein. As a non-limiting example, compounds display mitochondrial toxicity and/or cardiotoxicity if they cause direct or indirect injury to the mitochondria and/or cardiomyocyte comparable to that observed by any one of the various cardiotoxic compounds described herein.

The term "test compound" refers to a substance which is to be tested for cardiotoxicity in the assays of the invention. The test compound may be any kind of molecule such as a candidate drug, a chemical compound, a biological compound, organic or inorganic compounds, proteins, antibodies, environmental pollutants, a mixture of compounds, and the like.

DETAILED DESCRIPTION

The invention provides methods for predicting the cardiotoxicity of a compound, for example, in animal or human studies, by using an in vitro method. In addition the methods allow for screening for compounds and select suitable candidate, for further development, for example into a drug for (targeted) therapy. The selection may be based, in full or in part, on the results obtained with the method of to the invention and with respect to the observed potential cardiotoxic effect of the screened compound or compounds.

Furthermore, with the methods disclosed herein the person skilled in the art will be able to rank candidate drugs for their cardiotoxic potential and/or compare the cardiotoxic potential of a test compound with the cardiotoxic potential of a known cardiotoxic compound, either by direct comparison or based on previous results obtained with such compound.

The importance of recognizing the potential cardiotoxic effects of a test compounds is emphasized by the fact that nowadays humans are exposed to an increasing amount of non-physiological or non-natural compounds including pharmaceutical drugs and environmental toxicants. This is in addition to, for example, exposure to physiological relevant and naturally in the human body occurring compounds such as hormones, receptor ligands and/or second messengers. In other words, potential cardiotoxic effects of a compound in a living body, for example a human, may depend on the totality of factors present in a given body. However, as already detailed above, and as shown herein, the art comprises various examples that show that the available in vitro systems frequently fail to identify a compound as potential cardiotoxic, and only in the clinical setting the cardiotoxic effects are identified.

Most in vitro systems in the art are cell-based in vitro systems. In general a compound is provided to the cells and, using a suitable parameter, and the cells are examined for cardiotoxic effects (e.g. toxic effects on the mitochondria of the tested cardiomyocytes) imposed by the compound tested.

In the art in general use is made of primary cells, for example isolated from intact heart. Indeed primary cells isolated from intact heart have been an important model for study, however due to cell death and reproducibility the cells are in practice used only to a limited extend.

Although primary adult cardiomyocytes that can be used in in vitro assays may be obtained from various animals, including guinea pigs, rats, and mouse, successful culture of human cardiomyocytes has been more challenging. As a consequence, often use is made of non-human cells despite the differences in cardiac physiology and development between species.

In the course of experiments aimed at using cells of human origin, the inventors have now succeeded in identifying important aspect that influence the results of determining cardiotoxicity of a compound (e.g. toxic effects on the mitochondria of the tested cardiomyocytes). For this, the inventors tested compounds known to have an effect on cardiac functioning and identified important improvements in comparison to the methods described in the art. In particular, with the method of the invention a higher sensitivity was observed in comparison to methods in the art (see examples), which allows to identify potential or new cardiotoxic compounds that were not identified by the methods in the art.

In a first aspect there is provided for a method for predicting the cardiotoxicity of at least one test compound A, said method comprising:
(a) providing human stem-cell derived cardiomyocytes cultured in a medium comprising fatty acids and carnitine and not comprising glucose and/or galactose;
(b) treating the human stem-cell derived cardiomyocytes of step (a) with the at least one test compound A in the presence of a mitochondrial toxicant, preferably a cardiotoxic compound;
(c) examining the human stem-cell derived cardiomyocytes for the cardiotoxic effect resulting from the treatment of step (b) (e.g. toxic effects on the mitochondria of the tested cardiomyocytes); and
(d) comparing the results of step (c) with results obtained with control human stem-cell derived cardiomyocytes.

With the method the cardiotoxic effect (e.g. toxic effects on the mitochondria of the tested cardiomyocytes) of at least one test compound A can be determined or established. The cardiotoxic effect of a compound on the cells per se can be determined by studying the resulting effect of the compound on the cells used in the assay by applying any suitable assay for determining such effect, examples of which are provide herein.

The at least one compound to be tested may be one compound but may also be a mixture of different, related or unrelated compounds, for example a mixture of 1, 2, 3, 4, 5, 10, 100, 1000 or more compounds. It is also not required the structure of the compound, or of (part of) the compounds in the mixture are known. For example, the method may also be used to study the effect of mixtures of compounds, for example extracts obtained from plant material and the like. In addition pre-existing data with respect to the cardiotoxic effect of the compound or mixture of compounds may or may not be available.

The compound or mixture of compounds may be or comprise any kind of compound, including but not limited to candidate drugs, drugs, plant extracts, compounds isolated from nature, organic or inorganic compounds, food components, environmental pollutants, and include for example, proteins, antibodies, DNA molecules, RNA molecules and so on. Preferably the compounds can be exposed to the cell using an aqueous medium, preferably in which the compound shows at least some solubility, i.e. is soluble.

The skilled person understands that with the method, compounds may be identified that potentially will show cardiotoxic effects when administered to humans. The method is thus in particular suitable as a tool in establishing, for example the suitability of a candidate drug or drug combination, for further development and for example, as compared to other compounds or combinations of compounds tested.

In the method, advantage is taken of human stem-cell derived cardiomyocytes. Within the context of the invention, such human stem cell-derived cardiomyocytes refers to cardiomyocytes that are initially generated from pluripotent stem cells, for example from human pluripotent stem cells such as human embryonic stem cells, or from human induced pluripotent stem cells, by the process of differentiation. Thus the cells used in the method according to the invention are obtained by in vitro culturing, for example by in vitro differentiation of human pluripotent stem cells (including human induced pluripotent stem cells) and/or followed by in vitro maturation of the differentiated cells. Preferably the cells used in the method according to the invention are mature or matured cardiomyocytes obtained from human pluripotent or induced pluripotent stem cells.

After differentiation and/or maturation of the stem cells, and prior to use of the cells in the method of the invention, the cells are cultured in a suitable medium, and wherein the medium comprises fatty acids and carnitine, while at the same time does not comprise glucose and/or galactose. A medium as used herein refers to an aqueous solution, including buffers, suitable for maintaining human or animal cells for a sufficient period. For example, a medium is suitable if it allows the treatment of cells for a period required to obtain the effect intended by the treatment. The term "medium" also includes growth media that are suitable for the in vitro cell culture of human or animal cells. The medium may, in a preferred embodiment, be a defined medium, i.e. a medium suitable for the in vitro cell culture or maintenance of human or animal cells and in which all of the chemical components are known. Such defined medium does not or essentially not comprise any ill-defined source of nutrients and/or other ill-defined factors. Within the context of the current invention the defined medium (or medium) used may still contain defined amounts of products such as (purified) albumin, growth factors, and hormones, but is preferably essential free of serum (i.e. less than 1% w/w, preferably less than 0.5% w/w. even more preferably less than 0.1% w/w, even more preferably less than 0.05% w/w of the medium ready for use, most preferably the medium is free of serum (i.e. 0% w/w serum; albeit it might contain defined amount of specified compounds like (recombinant) albumin.

The medium may, depending on the state of the differentiated human pluripotent stem cells at the time the medium is provided to the cells, be a medium suitable for further differentiation of the cells into human cardiomyocytes, and/or for further maturing the differentiated cardiomyocytes into (more) mature cardiomyocytes, or, may be a medium suitable for maintaining the differentiated and/or matured cardiomyocytes.

Suitable (defined) media are known to the skilled person, and or can be easily adapted from those known from the prior art by, if so required, removing glucose and/or galactose from those media and/or adding fatty acids and creatine. Media that are suitable or can be easily adapted within the context of the current invention include, for example described in Mummery et al. Circ Res. 2012; 111(3):344-358, or Pluricyte medium (Pluriomics, Leiden, The Netherlands) and other as disclosed herein.

The skilled person understands he may further modify the media that is used to provide the human stem-cell derived cardiomyocytes to be used in the method of the invention. For example, additional compounds like thyroid hormone or a thyroid hormone analogue, preferably triiodothyronine or 3,5-diiodothyropropionic acid (DIPTA), may be added to the culture medium to further improve maturation of the cardiomyocytes, as can be witnessed from the electrophysiological characteristics of the thus obtained stem-cell derived cardiomyocytes.

Although in principal a stem-cell derived cardiomyocytes at any stage of development may be used in the method of the invention, preferably the stem-cell derived cardiomyocytes shows an embryonic, fetal, immature or mature state of development, i.e. they share characteristics with embryonic or fetal cardiomyocytes (in vivo, i.e. in a developing embryo or fetus) or, preferably, mature cardiomyocytes. The skilled person is well aware of the different stages of maturation phases of (human) stem cell-derived cardiomyocytes (see for a concise review Robertson et al. (StemCells 2013; 31:829-837).

Stem-cell derived cardiomyocytes showing such embryonic, fetal or immature state of development, i.e. such early phase stem-cell derived cardiomyocytes can, for example, be defined as contractile cells, with some proliferative capacity and with embryonic like electrophysiology (i.e., small negative membrane potential and small action potential amplitude). Late phase cells, or mature stem-cell derived cardiomyocytes can be defined by loss of proliferative capacity and a more adult human cardiomyocyte-like electrophysiology. Different elements of maturity appear to be affected by line, time in culture, co-cultured cells, and culture conditions. Adult cardiomyocytes may be large and cylindrical 'brick-like' (approximately 150*10 micrometer for ventricular cells), while embryonic and fetal cardiomyocytes are smaller with a reduced sarcomeric organization. Similarly, early phase stem-cell derived cardiomyocytes are small and round to slightly oblong (e.g. approximately 5-10 micrometer diameter), whereas late phase stem-cell derived cardiomyocytes develop a more oblong morphology. In general early phase stem-cell derived cardiomyocytes proliferate at a lower rate than their pluripotent progenitors whereas late phase stem-cell derived cardiomyocytes can be considered non-proliferating cells. The transcriptional profile of stem-cell derived cardiomyocytes is different from their originating pluripotent stem cells and well-known differences include loss of pluripotency transcription factors and up regulation of cardiac markers). The metabolic maturity can be determined by methods known to the skilled person, for examples methods that look at phenotype, morphology, gene expression, metabolic markers, cell surface markers, electrophysiological characteristics and/or cellular functional assay of the cell. For example, for maturation one can determine decreased expression of genes associated with a "fetal" state or cardiac hypertrophyic state such as, for example, NPPA (BNA) and NPPB (BNP), or preferably, determine the electrophysiological characteristics of the maturing stem-cell derived cardiomyocytes, and wherein a more adult cardiomyocyte characteristic can be seen for more maturated stem-cell derived cardiomyocytes, as discussed in detail herein.

In addition the relative maturity of stem-cell derived cardiomyocytes can be determined by the presence of decreased expression of genes associated with the a fetal state, such as NPPA, NPPB, smooth muscle actin and skeletal actin, or the increasing expression of adult genes/proteins, such as myosin light chain 2V, calsequestrin and ryanodine receptor).

Thus, the stem-cell derived cardiomyocytes to be provided for use in the method of the invention shows an embryonic, fetal, immature or mature state of development; as mentioned above, the cells preferably sho a mature state of development.

As mentioned above, the cells are cultured in a medium comprising fatty acids and carnitine while at the same time not comprising glucose and/or galactose. It was surprisingly found that when in the method of the invention human stem-cell derived cardiomyocytes were provided that were cultured in a medium that is devoid of glucose and/or galactose but that does comprise fatty acids and carnitine, the method allows for more sensitive measurement of the cardiotoxicity of a compound (e.g. toxic effects on the mitochondria of the tested cardiomyocytes), for example in comparison to the same method, but wherein the human stem-cell derived cardiomyocytes that have been used where cultured in a medium directly prior to performing the assay, i.e. directly before performing step (b) as described above (treating the cells with the at least one test compound).

Thus the medium used to obtain the human stem-cell derived cardiomyocytes to be provided for use in the method of the invention is cultured in a medium not comprising glucose, not comprising galactose, or not comprising glucose and galactose. Preferably the medium does not comprise glucose, more preferably the medium does not comprise glucose and galactose. It is understood by the skilled person that very low levels, i.e. too low to act as the sole carbon source for the cells, is, within the context of the current invention may be considered as being a medium that does not comprise glucose and/or galactose. However, preferably the medium is free of glucose and/or galactose, preferably both.

The period that is required for the cells to be provided for use in the method of the invention (i.e. the cells that are provided in step (a)) is not limited in time and depends in part on the metabolic activity of the cells and the levels of glucose and/or galactose present after addition of a medium that does not comprise glucose and/or galactose, but does comprise fatty acids and carnitine. For example, cells that are metabolically active may deplete remaining glucose and/or galactose sources in a shorter period of time. As a consequence such cells will adapt to the fatty acids and carnitine in the medium after a shorter period of time in the medium without the galactose and/or glucose and may thus require a shorter period of culture/incubation before performing the remainder of the method of the invention.

The fatty acids comprised in the medium may be any type of fatty acids source (including monoglycerides, diglycerides and or triglycerides comprising fatty acid chains). With respect to the concentration of fatty acids present in the medium without glucose and/or galactose, said concentration can be readily established by the skilled person. The concentration of fatty acids must be as such that during the period in which the method of the invention is performed no substantial cell death is induced as a consequence of a lack of fatty acids. In practice the medium used in the method according to the invention comprises about 0.1 microM to 1 mM fatty acids, preferably 0.5-500 microM, preferably 1-100 microM, even more preferably 1-15 microMolar fatty acid. Preferable the fatty acids comprised in the medium comprises at least one, two or three of linolenic acid, linoleic acid and palmitic acid. Preferably a mixture of different fatty acids is used.

Preferably the medium further comprises cholesterol, preferably about 1 microgram/ml to about 4 microgram/ml of cholesterol.

In addition to the fatty acids, the medium without glucose and/or galactose also comprises carnitine, preferably the composition comprises about 0.5 mM to about 3.5 mM of carnitine.

In one embodiment, the method according to the invention also involves the culturing of stem cells to obtain the human stem-cell derived cardiomyocytes, and as described above.

In a next step of the method of the invention, the provided human stem-cell derived cardiomyocytes are treated with the at least one test compound A, in the presence of a mitochondrial toxicant, preferably a cardiotoxic compound. The human stem-cell derived cardiomyocytes are thus incubated in the presence of not only the at least one compound A for which the cardiotoxicity (e.g. toxic effects on the mitochondria of the tested cardiomyocytes) needs to be determined but at the same time in the presence of a mitochondrial toxicant, preferably a cardiotoxic compound. It was surprisingly found that by performing the incubation of the at least one compound in the presence of a mitochondrial toxicant, preferably a cardiotoxic compound, the sensitivity of the assay is increased (see examples). In other words, the difference in a parameter indicative for cardiotoxicity (e.g. toxic effects on the mitochondria of the tested cardiomyocytes) between the control situation and the test situation is increased. Compounds that may be considered non-cardiotoxic in an assay in the art may turn out to be cardiotoxic based on the method of the invention. This was confirmed for example for the monoclonal antibody trastuzumab (see examples). In other words, compounds when tested in stem cell derived cardiomyocytes cultivated on glucose and/or galactose comprising medium may show only no or very limited cardiotoxic effects (e.g. mitochondrial toxicity in the stem cell derived cardiomyocytes). Likewise, compounds when tested in stem cell derived cardiomyocytes cultivated on a medium without glucose and/or galactose may show only no or very limited cardiotoxic effects (e.g. mitochondrial toxicity in the stem cell derived cardiomyocytes). In contrast, such compounds when tested in stem cell derived cardiomyocytes cultivated on a medium without glucose and/or galactose but comprising carnitine and fatty acids, and when tested in the presence of a mitochondrial toxicant, may show significant and important cardiotoxic effects (e.g. mitochondrial toxicity in the stem cell derived cardiomyocytes).

The concentration of test compounds used for the assays in the present invention will vary depending upon the nature of the compound, the length of time that the test compound is exposed to the cells and the amount of cells. In typical assays performed by the inventors, the concentration of the test compound closely resembles the intended therapeutic concentration, and which may, for example, range from 100 pM to 100 micro M for example 1 nM to 500 nM. In general a lower concentration of the test compound may be used with increasing exposure time. It is understood that also concentration ranges may be employed using the assays of the invention. It is also understood that test compound concentrations higher or lower than the concentrations disclosed herein may also be used. The person skilled in the art has no problem in determining suitable concentrations or concentration ranges for testing in the method of the invention.

Also the concentration of the mitochondrial toxicant, preferably a cardiotoxic compound, used for the assay in the present invention will vary depending upon the nature of the compound, the length of time that the test compound is exposed to the cells and the amount of cells. In typical assays performed by the inventors, the concentration of the mitochondrial toxicant, preferably cardiotoxic compound, used may range from 50 nM to 500 μM, for example 100 nM to 100 μM. In general a lower concentration of the test compound may be used with increasing exposure time. It is understood that concentration ranges may also be employed using the assays of the invention. It is also understood that concentrations higher or lower than the concentrations disclosed herein may also be used. The person skilled in the art has no problem in determining suitable concentrations or concentration ranges for the mitochondrial toxicant to be used in the method of the invention.

The skilled person understands that the compound A to be tested and the mitochondrial toxicant are, in the same experiment, not the same compounds.

The treatment of the human stem-cell derived cardiomyocytes with the at least one test compound A in the presence of a mitochondrial toxicant, preferably a cardiotoxic is performed in a suitable medium. Preferably the medium is a medium that does not comprise glucose and/or galactose, as described above. Preferably the medium does comprise fatty acids and carnitine, as described above. Preferably the medium does not comprise glucose and galactose but does comprise fatty acids and carnitine, as described above. Preferably the medium is the same medium that was used to provide the human stem-cell derived cardiomyocytes in step (a).

The period that is required for the treatment with the at least one compound A in the presence of a mitochondrial toxicant is not limited in time and depends in part on the metabolic activity of the cells, the type of compound and so on. Based on the disclosure herein, the skilled person will have no problem in establishing a suitable period of incubation.

It also understood that the method of the invention is not limited to treating with the at least one compound in the presence of one mitochondrial toxicant. Also contemplated is the use of different mitochondrial toxicant, either in separate, simultaneous of sequential experiments or as mixtures of, for example, one, two, three or more mitochondrial toxicants. For example, mitochondrial toxicants with possible different modes-of-action by be used, alone, sequential, simultaneously or in a mixture.

The method of the invention may also allow for determining the effect (inhibitory or stimulatory) of a first compound on the cardiotoxic effect (e.g. toxic effects on the mitochondria of the tested cardiomyocytes) of a second compound, and vice versa.

In a next step, after treatment of the human stem-cell derived cardiomyocytes with the test compound, the treated human stem-cell derived cardiomyocytes are examined for the cardiotoxic effect (e.g. toxic effects on the mitochondria of the tested cardiomyocytes) resulting from the treatment performed in step (b). The method of the invention is not limited to a specific test for determining the cardiotoxic effects that were imposed by the treatment. The skilled person is aware of different types of assays and methods that may be used to establish cardiotoxic effects imposed in cardiomyocytes (and for example as disclosed herein).

Examining may be relative to control experiments, for example by comparing using human stem-cell derived cardiomyocytes that were cultured in a medium that does comprise glucose and/or galactose, and/or by comparison to a treatment with only the test compound, and without the presence of the mitochondrial toxicant, or both, and or in the presence or absence of further compounds and ligands as disclosed below. Again, the skilled person will have no problem in devising the appropriate experimental controls.

Indeed, in a final step the results of step (c) are compared with results obtained with control human stem-cell derived cardiomyocytes. This may be results obtained from experiments performed in the past, but preferably the control human stem-cell derived cardiomyocytes are derived from the same batch of human-stem cell derived cardiomyocytes provide in step (a) in order to exclude any culturing effect between different experiments. For example, the cells for the test situation and the control situation may be cultured and treated concurrent or simultaneously, albeit in separate dishes or well or culture flasks. An increase in the indication of a cardiotoxic effect (e.g. toxic effects on the mitochondria of the tested cardiomyocytes) as established by the examining step (c) indicates increased cardiotoxic effects of the tested compound (and/or combination).

In a preferred embodiment, the control human stem-cell derived cardiomyocytes are cardiomyocytes that are or have been cultured in a medium, preferably the same medium, comprising the mitochondrial toxicant of step (b) and not comprising the at least one test compound A of step (b). The method of the present invention enables discovery of compounds (compound A) which when tested on their own (i.e. in absence of the mitochondrial toxicant) would escape detection as a cardiotoxicant in traditional methods, as described in the art, for example as these would in such assays not cause sufficient mitochondrial dysfunction or because these assays do not assess mitochondrial toxicity of a test compound, and are, for example based on crude, non-sensitive measurements, for example based on survival rate only.

In particular the combination of using cells cultured in the absence of glucose and/or galactose and testing in the presence of a mitochondrial toxicant provides for an improved method of predicting cardiotoxicity, compared to methods not employing such combination of measures.

As stated before, the at least one compound A may be any type of compound that requires testing. In a preferred embodiment the at least one compound is a receptor ligand for at least one receptor, preferably for one receptor, a modulator of a kinase a modulator of a phosphatase, and/or a modulator of an enzyme. Preferably the at least one compound A is a receptor ligand for a cell surface receptor; i.e. for a receptor that is expressed at the cell surface of a (human) cell.

The skilled person understands these terms. For example, and within the context of the invention, a ligand is a substance or compound that may form a complex with a biomolecule, for example a receptor, to serve a biological purpose, for example to activate or the deactivate a certain biological function. One example is activation of a signaling cascade. Within the context of the current invention, the receptor is normally a protein, preferably a membrane protein, even more preferably a cell surface protein (receptor). In certain circumstances a ligand by be a ligand for binding to DNA.

A modulator is a compound that may bind to, inhibit or activate a protein, for example to an enzyme (i.e. a protein with catalyst activity), a kinase (an enzyme that transfers phosphate groups from high-energy, phosphate-donating molecules to specific substrates, normally other proteins), or a phosphatase (which remove phosphate groups). In particular these biological macromolecules are often targets for the development of drugs while in addition these molecules may exert or modulate a wide range of biological activities and functions in a wide range of different cells in the body.

In particular testing compounds that are designed to be a ligand for such receptor and/or an modulator of such enzyme, kinase or phosphatase is advantageous with the method of the invention, in particular for ligands for cell surface receptors.

As stated above, the modulator may be an activator, inhibitor or deactivator of an enzyme, kinase or phosphatase. The skilled person understands that it may also be an activator for one type of enzyme and an inhibitor for another type.

In a further preferred embodiment the enzyme, kinase of phosphatase is expressed by the human stem-cell derived cardiomyocytes that are used in the method of the invention. Such expression may be either natural expression or induced expression (e.g. by environmental triggers) but also as the consequence of genetic modification of the cells, including the introducing of expression vectors.

In a further preferred embodiment the receptor, preferably the cell surface receptor, is expressed by the human stem-cell derived cardiomyocytes. Such expression may be either natural expression or induced expression (e.g. by environmental triggers) but also as the consequence of genetic modification of the cells, including the introducing of expression vectors. Although expression is preferred, the skilled person understand it is not required for determining the cardiotoxic effect of a compound A per se.

Also disclosed is that the at least one test compound is an antibody, preferably a human antibody, preferably a monoclonal human antibody. Within the context of the current invention antibodies also include, next to classical antibodies, nanobodies, single-domain antibodies, humanized antibodies, single-chain antibodies and compound comprising such antibodies.

It will be understood by the skilled person that various incubation schemes are possible within the context of the current invention. For example the cells may be pre-incubated in the presence of the mitochondrial toxicant followed by incubation with both the test compound A and the mitochondrial toxicant. Alternatively the cells are pre-incubated with the test compound, followed by incubation in the presence of both the test compound and the mitochondrial toxicant. Another example is that the cells are not pre-incubated by treated only with the test compound A and the mitochondrial toxicant at the same time.

In a further embodiment of the method of the invention, and wherein the at least one test compound is a receptor ligand for at least one receptor, a modulator of a kinase, a modulator of a phosphatase, or a modulator of an enzyme, the human stem-cell derived cardiomyocytes are cultured in step (a) and/or treated in step (b) in the presence of, respectively, a further receptor ligand for the at least one receptor, a further modulator of the kinase, a further modulator of the phosphatase, a further modulator of the enzyme.

In this embodiment, and when for example the test compound A is a ligand for a cell surface receptor, it was found it is advantageous to either culture the cells to be provided in step (a) or to treat the cells in step (b) in the presence of another (or more), in this example, receptor ligand for the same receptor. Preferably the other, in this example, receptor ligand, in a ligand that is naturally occurring in the human body i.e. that is normally produced in an used by the human body as a ligand for the receptor to which the test compound A is also a ligand. Preferably the further ligand or modulator, preferably naturally occurring in the human body, is both used to culture the cells to be provided in step (a) and to treat the cells with the test compound A in step (b). In such embodiment, the treatment in step (b) with the at least one compound is in the presence of the mitochondrial toxicant and in the presence of a further modulator and/or ligand. Preferably, but not necessarily, in case the compound A is an inhibitor, the further modulator is also an inhibitor. The same logic applies in case of an activator and/or with respect to the ligand for a receptor.

The concentration of further ligand or modulator used for the assays in the present invention will vary depending upon the nature of the compound, the length of time that the test compound is exposed to the cells and the amount of cells. In typical assays performed by the inventors, the concentration of the test compound used may range from 100 pM to 100 micro M for example 1 nM to 500 nM. In general a lower concentration of the further ligand or modulator may be used with increasing exposure time. It is understood that concentration ranges may also be employed using the assays of the invention. It is also understood that concentrations higher or lower than the concentrations disclosed herein may also be used. The person skilled in the art has no problem in determining suitable concentrations or concentration ranges for use in the method of the invention.

In case the test compound A is a ligand of a modulator, the compound is preferably a agonist, partial agonist, antagonist, inverse agonist or an allosteric modulator of said at least one receptor; and/or an inhibitor or stimulator of said kinase, phosphatase and/or enzyme. The skilled person is aware of the common general meaning of these terms.

The person skilled in the art is aware of methods available in the art to determine or measure cardiotoxic effects (e.g. toxic effects on the mitochondria of the tested cardiomyocytes) and/or mitochondrial toxicity as a consequence of the method of treatment with the test compound A as disclosed herein. In other words, the skilled person is well aware of the method to determine cardiotoxicity in step (c) of the method disclosed herein. For example, methods that measure disrupted energy Metabolism and/or free radical generation and/or altered apoptosis may suitably be used in the method according to the invention (see Dykens et al (2007) Drug Discovery Today 12:17-18:777-785). Others included assays for ATP production, membrane potential, caspase 3 activation, PARP activation (apoptosis), oxygen consumption, mitochondrial biogenesis, OXPHOS Enzyme Activity Assays, assays for reactive oxygen species. In a preferred embodiment however, the method is selected from the group consisting of methods determining ATP levels in the cell, basal respiration of the cells, ATP turnover, proton leak and/or maximal respiration. Also suitable are the so-called MitoSciences (Eugene, Oregon, USA) assays which are able to measure the activity and expression of key metabolic enzymes, plus their phosphorylation and acetylation, to elucidate effects on energy metabolism. They can measure protein specific nitration and carbonylation to elucidate effects from oxidative stress, and they can measure changes in expression and translocation within the cell of key pro- and anti-apoptotic proteins.

The medium used either for obtaining the cells to be provided in step (a) of the method disclosed herein and/or for treating the cells in step (b) of the method disclosed herein may be any suitable medium that is free of glucose and/or galactose, preferably free of glucose or free of galactose or free of glucose and galactose and comprises fatty acids and carnitine. The skilled person understands that it is not necessary that the medium used in step (a) and the medium used in step (b) are identical, although it is preferred that the medium used in both steps are the same (except for the presence of the test compound and/or mitochondrial toxicant and/or the further compound, i.e. ligand). However in a preferred embodiment the medium comprises:

A basal medium without glucose and/or galactose, preferably 80-99 (vol/vol) % DMEM-glucose (e.g. Gibco 21056), preferably 92-95%, most preferably 95%.;

0.05-5 mM L-carnitine (e.g. Sigma CO283), preferably 1-4 mM, most preferably 4 mM; and 0.1 microM (micromolar) to 1 mM fatty acids, preferably 0.5-500 microM, preferably 1-100 microM, even more preferably 1-15 microMolar fatty acid, preferably from 100* Chemically defined lipids Gibco 11905). The fatty acid source may be one type of fatty acid, but may also be a mixture of fatty acids, for example, selected from Arachidonic Acid, Linoleic Acid, Linolenic Acid, Myristic Acid, Oleic Acid, Palmitic Acid, Palmitoleic Acid and Stearic Acid. In a preferred embodiment 100* Chemically defined lipids Gibco 11905 is used in a 1:20-1:1000, preferably 1:50-1:250, most preferably 1:100 dilution (vol/vol) relative to the total medium.

In a preferred embodiment the medium further comprises glutamine (preferably in a final concentration of 0.5-5 mM, most preferably 1-3 mM, e.g. 2 mM), for example in the form of L-alanyl-L-glutamine dipeptide (Glutamax; e.g. Gibco 35050) (preferably in a final concentration of 0.5-5 mM, most preferably 1-3 mM, e.g. 2 mM), and/or Insulin-Transferrin-Selenium-Ethanolamine (preferably the concentration used of each of the compounds is equivalent to a 1:50-1:250, preferably 1:100 dilution in the total medium of a concentrate comprising 1 g/L insulin, 0.55 g/l transferrin, 0.00067 g/l sodium selenite and 0.20 g/l ethanolamine (e.g. 100* ITS-X Gibco 51500), and/or alpha-monothioglycerol (100-600 nM, preferably 400-500 nM, for example 450 nM), and/or ascorbic acid (preferably 0.01-0.2 mg/ml total medium, most preferably 0.03-0.08 mg/ml, for example 0.05 mg/ml), and/or trace elements (preferably equivalent to 1:5000-1:20000, for example 1:10000 dilution in the total (final) medium of 1000* Trace element mix B of Cellgro 99-176-CL and 1:500-1:2000, for example 1:1000 dilution in the total (final) medium of 1000* Trace elements Mix C of Cellgro 99-176-CLO), and/or creatine (preferably 0.05-20 mM creatine, most preferably 2-7 mM creatine, for example 5 mM), and/or taurine creatine (preferably 0.05-20 mM, most preferably 2-7 mM, for example 5 mM). Preferably all of the above are included in the medium.

In case for example Thyroid hormone is used in the medium, preferably 50-100 nM, most preferably 70-80 nM, for example 74 nM thyroid hormone is present tin the medium.

In general, and preferably, the medium without glucose and/or galactose as used in the method according to the invention does not comprise any additional growth factors and compounds known from the prior art relating to obtaining and or culturing stem-cell derived cardiomyocytes, such as BMP, IGF, FGF, TGFbeta and/or wnt-inhibitors and the like and/or small molecules targeting the differentiation and/or maturation of human (induced) pluripotent stem cells derived cardiomyocytes. However, the medium without glucose and/or galactose used in the method according to the invention may in certain embodiments be supplemented with such growth factors and/or compounds. In a particular preferred embodiment the cells to be used in the method according to the invention are such cells as are commercially available from Pluriomics (e.g. Pluricyte Cardiomycoytes) (Leiden, The Netherlands; www.pluriomics.com). Such and other cells may be provided as cryopreserved cells and initially cultivated on a medium comprising glucose and/or galactose for recovery (for example Pluricyte medium, Pluriomics, Leiden, The Netherlands). Afterwards the cells are cultivated on the medium without glucose and/or galactose but comprising fatty acids and carnitine, as detailed herein.

In an even further preferred embodiment the medium is further free of serum albumin.

In a preferred embodiment the human stem-cell derived cardiomyocytes that are provided in step (a) are obtained by proliferating human stem-cells in a first medium, followed by maturating the obtained cells in a second medium followed by culturing the cells in a third medium, and wherein said third medium is a medium comprising fatty acids and carnitine and not comprising glucose and/or galactose, preferably wherein the cells are cultured in the third medium for a period of at least 24-48 hours.

The first and second medium may be any suitable medium available in the prior art, for example as described in WO2014200339. The first and second medium may comprise glucose. The maturation medium (second medium) may comprise, for example, thyroid hormone. The third medium may also be any suitable medium but is preferably a medium as described in detail herein.

As discussed herein, the period during which the cells to be provided in step (a) are cultured in the medium comprising fatty acids and carnitine, and not comprising glucose and/or galactose can, in view of the current disclosure easily be established by the skilled person. In a preferred embodiment however the human stem-cell derived cardiomyocytes provided in step (a) were cultured in said medium without glucose or galactose for a period of between 12-120 hours, preferably 12-96 hours, more preferably 12-60 hours, most preferably 24-48 hours. It is understood by the skilled person that when a further ligand and/or modulator (as described herein, for example in claim 5 as filed) is present in the culture medium used to provide the human stem-cells derived cardiomyocytes in step (a), as detailed herein, such ligand or modulator is present in the culture medium for at least part, but preferably the same period, as the medium without glucose and/or galactose but comprising fatty acids and carnitine Prior to culturing of the human stem-cell derived cardiomyocytes to be provided in step (a) in a culture medium comprising fatty acid and carnitine and not comprising glucose and/or glucose, the cells may be cultured in any type of suitable medium, including a medium that does comprise glucose and/or galactose.

As detailed herein, the period of treatment in step (b) can be established by the skilled person without undue burden. In a preferred embodiment, the human stem-cell derived cardiomyocytes are treated in step (b) for a period of between 12-120 hours, preferably 12-96 hours, more preferably 12-60 hours, most preferably 24-48 hours. Preferably the at least one compound A, the mitochondrial toxicant and, optionally the further ligand and/or modulator are present at the same time and during the full period of treatment. However it is also contemplated that the at least one compound A, the mitochondrial toxicant and, optionally the further ligand and/or modulator are added sequentially to the medium used to treat the cells.

As detailed herein, the mitochondrial toxicant may be any kind of known mitochondrial toxicant, for example, but not limited to drugs like Valproate (Depakote), Amitriptyline (Elavil), Amoxapine, Fluoxetine (Prozac), Citalopram (Cipramil), Chlorpromazine (Thorazine), Fluphenazine (Prolixin), Haloperidol (Haldol), Resperidone (Risperdol), Phenobarbital, Secobarbital (Seconal), Butalbital (Fiorinal), Amobarbital (Amytal), Pentobarbital (Nembutal), Alprazolam (Xanax), Diazepam (Valium, Diastat), Statins, Bile acids-cholestyramine, Ciprofibrate, Fenofibrate, Aspirin, Acetaminophen (Tylenol), Indomethacin (Indocin), Naproxen (Aleve), Diclofenac, Tetracycline, minocycline, Chloramphenical, Aminoglycosides, Linezolid (Zyvox), Amiodarone, Interferon, Zidovudine, Doxorubicine (Adriamycin), Cis-platinum, Tamoxifen, and Metmorfin and/or those disclosed in Dykens et al (Drug Discovery Today (2007): 12 (17/18): 777-785, in particular Box 1, including celecoxib, diclofenac, ibuprofen, indomethacin, mefenamic acid, meloxicam, naproxen, piroxicam, sulindac, tamoxifen, atenolol, amiodarone, amphetamines, bupivacaine, pioglitazone and/or rosigliatizone. However preferably the mitochondrial toxicant is selected from the group consisting of anthracyclines including doxorubicin, daunorubicin, epirubicin, idarubicin, valrubicin, and mitoxantrone, and combinations thereof.

In another preferred embodiment the at least one receptor is the human ERBB2 receptor. This receptor is well known to the skilled person and is targeted by the monoclonal antibody trastuzumab (Herceptin). In a preferred embodiment, the receptor is a receptor that is targeted by trastuzumab.

In another preferred embodiment the further receptor ligand in neuregulin. Neuregulins are known to the skilled person. Neuregulins are a family of four structurally related proteins that are part of the EGF family of proteins. Preferably the neuregulin is heregulin, also referred to as neuregulin 1, and that interacts with the human ERBB2 receptor.

In another embodiment, the method of the invention, i.e. steps (a)-(d) are repeated but wherein the human stem-cell derived cardiomyocytes provided in step (a) were cultured in a medium comprising glucose and/or galactose.

Also provided is a method for screening compounds for cardiotoxicity (e.g. toxic effects on the mitochondria of the tested cardiomyocytes), said method comprising
(a) Providing a plurality of test compounds and providing human stem-cell derived cardiomyocytes cultured in a medium comprising fatty acids and carnitine and not comprising glucose and/or galactose;
(b) Treating the human stem-cell derived cardiomyocytes of step (a) with each test compound in the presence of a mitochondrial toxicant, preferably a cardiotoxic compound;
(c) Examining the human stem-cell derived cardiomyocytes for the cardiotoxic effect resulting from the treatment of step (b) (e.g. toxic effects on the mitochondria of the tested cardiomyocytes);
(d) Comparing the results of step (c) with results obtained with control human stem-cell derived cardiomyocytes Preferences and details as disclosed herein are likewise applicable to the aspect of the invention.

In another aspect there is provided for a kit comprising human stem-cell derived cardiomyocytes, the medium without glucose and/or galactose and comprising fatty acids and carnitine as defined in any one of claims 1-16 as filed, and, optionally a mitochondrial toxicant. Preferably the human stem-cell derived cardiomyocytes are human stem-cell derived cardiomyocytes that were cultured in a medium not comprising glucose and/or galactose but comprising fatty acids and carnitine.

The skilled person understands that any embodiment or preference detailed herein may be combined with any other embodiment or preference described.

EXAMPLES

Example 1

Culture and Differentiation hESC were cultured in stem cell medium on mitotically inactivated mouse fibroblasts and passaged using TrypLE Select (Invitrogen). Stem cell medium contains DMEM/F12 (Gibco, cat. no. 11320-033), 20% (v/v) knockout serum replacement (Gibco, cat. no. 10828-028), 10 mM non-essential amino acids (Gibco, cat. no. 11140-050), 2 mM L-glutamine (Gibco, cat. no. 25030-081) 2beta-mercaptoethanol (Gibco, cat. no. 21985-023), and 10 ng/ml human basic FGF.

One day before differentiation, cells were passaged onto matrigel coated 6-well plates at a density of 1 million cells/well in stem cell medium.

Cells were differentiated in embryoid bodies. At day 0, cells were collected and resuspended at 6×104 cells ml-1 in Differentiation medium (46.5% IMDM (Gibco 21056), 0.25% Bovostar BSA, 46.5% Ham's F12 with Glutamax, 0.125% polyvinylalcohol (MR103), 1% 100*Chemically defined lipids (Gibco 11905), 2 mM GLutamax, 0.1% 100* ITS-X (Gibco 51500), 450 nM alphaMTG, 0.05 mg/ml ascorbic acid, 0.5% 5000 U/ml Pen/Strep (Gibco 12070), 0.01% 1000* Trace elements mix B (Cellgro 99-176-CL), 0.1% 1000*Trace elements mix C (Cellgro 99-176-CL)) containing 20 ng ml-1 of BMP4 (R&D Systems) and 30 ng ml-1 activin A (R&D Systems), 30 ng ml-1 VEGF (R&D systems), 40 ng ml-1 SCF (R&D systems) and 1.5 µM Chir99021 (Axon medchem); 50 µl of this mix was placed into each well of a 96-well round-bottom non-adherent plate yielding EBs composed of 3,000 cells. On day 3, 7, 10, 14 and 17 the medium was replaced with differentiation medium without growth factors. Contracting cardiomyocytes can be induced for further differentiation by treating the cells with specialized media like Pluricyte media (Pluriomics The Netherlands) or long term culture.

ATP Assays

Cells were dissociated at day 21 using 10× TrypLE select and replated at 20.000 cells/well in white 96-well plates (Corning 655098) and treated according to the protocol shown in FIG. 1. Alternatively, Pluricyte Cardiomyocytes were obtained from Pluriomics (Leiden, The Netherlands). The cryopreserved cells were recovered in maintained in Pluricyte Medium (Pluriomics, Leiden, The Netherlands) and thereafter cultivated on medium without glucose and/or galactose but comprising fatty acids and carnitine as described below.

In short, cells were, in this example, first cultivated in CM (cardiomycocyte medium comprising 46.5% IMDM (Gibco 21056), 0.25% Bovostar BSA, 46.5% Ham's F12 with Glutamax, 0.125% polyvinylalcohol (MR103), 1% 100*Chemically defined lipids (Gibco 11905), 2 mM GLutamax, 1% 100* ITS-X (Gibco 51500), 450 nM alphaMTG, 0.05 mg/ml ascorbic acid, 0.5% 5000 U/ml Pen/Strep (Gibco 12070), 0.01% 1000* Trace elements mix B (Cellgro 99-176-CL), 0.1% 1000* Trace elements mix C (Cellgro 99-176-CL), 2 mM carnitine (Sigma C0283), 5 mM creatine (Sigma C3630), 5 mM Taurine (Sigma T8691)) for a period of 5 days (As discussed above, the medium may comprise any additional compounds like growth factors or small molecules that target differentiation and/or maturation of the human stem cell derived cardiomyocytes, for example wnt-inhibitors and the like). At day 5 medium was replaced by medium without glucose and/or galactose and with fatty acids and carnitine (CM– medium comprising 93% DMEM—glucose (Gibco 11966), 0.125% polyvinylalcohol (MR103), 1% 100*Chemically defined lipids (Gibco 11905), 2 mM Glutamax, 1% 100* ITS-X (Gibco 51500), 450 nM alphaMTG, 0.05 mg/ml ascorbic acid, 0.5% 5000 U/ml Pen/Strep (Gibco 12070), 0.01% 1000* Trace elements mix B (Cellgro 99-176-CL), 0.1% 1000* Trace elements mix C (Cellgro 99-176-CL), 2 mM carnitine (Sigma C0283), 5 mM creatine (Sigma C3630), 5 mM Taurine (Sigma T8691)). Depending on the experimental goal, to this CM– medium and at this stage, for example the mitochondrial toxicant may be added, and/or the further receptor ligand, further modulator of the kinase, phosphatase or enzyme, for example, as used in various of the examples herein, 10 ng/ml neuregulin).

After two days to the medium the compound A to be tested is added, together with the mitochondrial toxicant and/or the further receptor ligand, further modulator of the kinase, phosphatase or enzyme as described above in detail. In the current example, doxorubicin and compound A in the form of an antibody were added.

After two days, an ATP viability assay was performed. ATP values were measured using the Promega Cell titer Glo luminescent cell viability kit according to manufacturers instructions. Briefly CellTiter-Glo reagent is added to the cells which causes the cells to lyse. Available ATP is measured via an ATP dependent conversion of Luciferin by a recombinant Luciferase, which produces oxyluciferin and light. The amount of luminescence generated is therefore directly proportional to the amount of ATP in the cells.

Results

The results are shown in the accompanying figures.

Figure 2:
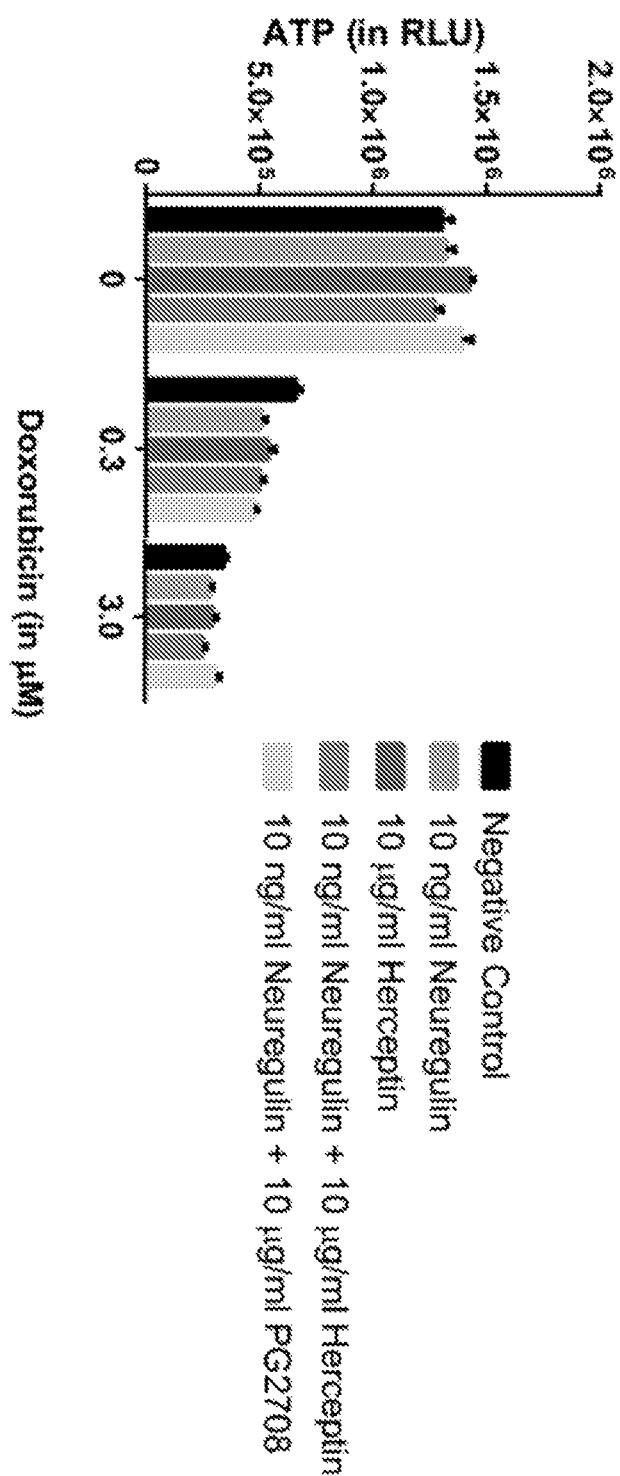
FIG. 2 shows the results of Promega ATP assay on cardiomyocytes that were cultivated in the presence of glucose and treated with various concentrations of the mitochondrial toxicant doxorubicin in the presence of neuregulin, herceptin, neuregulin+herceptin, and neuregulin+ control antibody. Although doxorubicin shows a clear effect on ATP levels, none of the other treatments seems to affect this (n=6)

FIG. 2 shows the results of Promega ATP assay on cardiomyocytes that were cultivated in the presence of glucose and treated with various concentrations of the mitochondrial toxicant doxorubicin in the presence of neuregulin, herceptin, neuregulin+herceptin, and neuregulin+control antibody. Although doxorubicin shows a clear effect on ATP levels, none of the other treatments seems to affect this (n=6)

Figure 3:
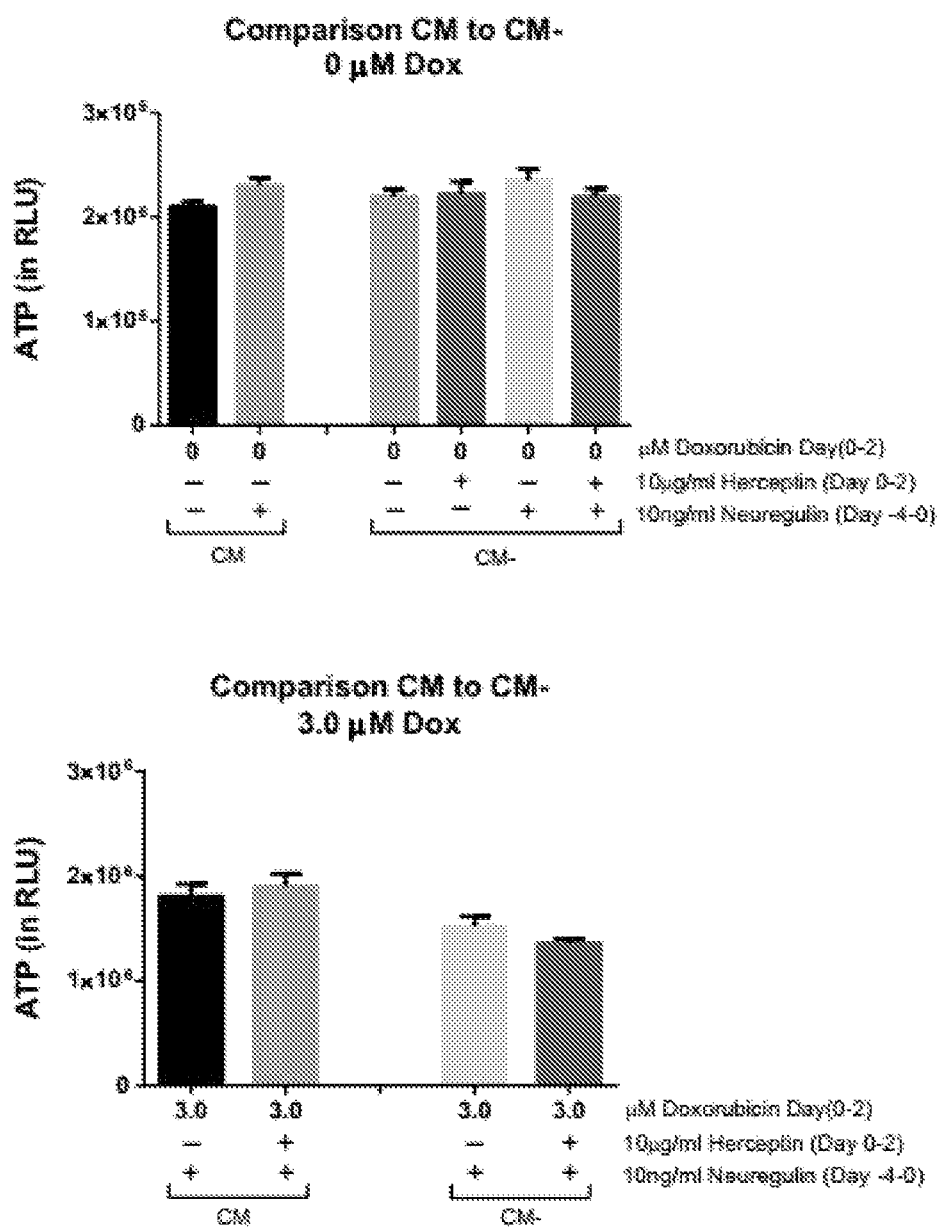
FIG. 3 is a comparison of cells grown in CM (medium with glucose) and CM− (medium without glucose and galactose but with fatty acids and carnitine. The upper panel shows that cells in CM and CM− have similar ATP levels. The lower level shows that the mitochondrial toxicity by doxorubicin is more pronounced in cells cultured in CM− illustrating their dependence upon mitochondrial oxidative phosphorylation.

FIG. 3 is a comparison of cells grown in CM (medium with glucose) and CM− (medium without glucose and galactose but with fatty acids and carnitine. The upper panel shows that cells in CM and CM− have similar ATP levels. The lower level shows that the mitochondrial toxicity by doxorubicin is more pronounced in cells cultured in CM− illustrating their dependence upon mitochondrial oxidative phosphorylation.

Figure 4:
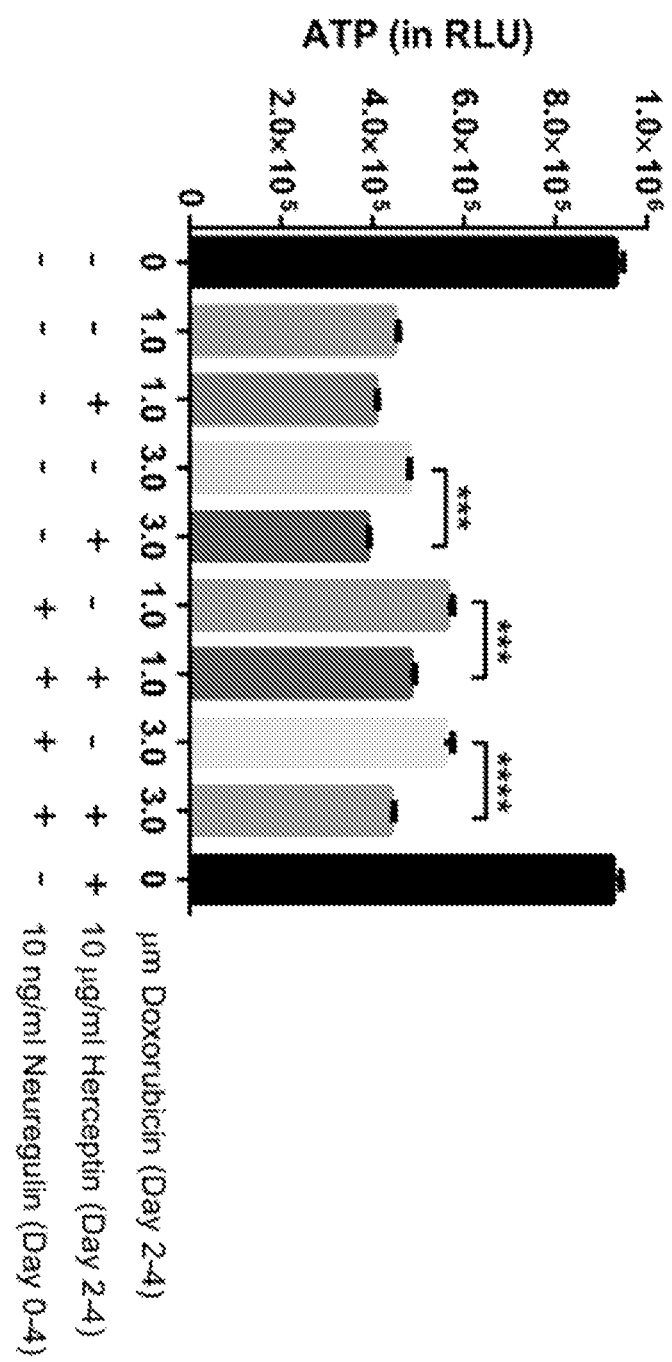
FIG. 4 shows that addition of the Neuregulin ligand improves the robustness of the assay showing effects of Herceptin at both doxorubicin concentrations tested. Neuregulin is the natural ligand for the HER2 receptor.(p-values as in FIG. 5).

FIG. 4 shows that addition of the Neuregulin ligand improves the robustness of the assay showing effects of Herceptin at both doxorubicin concentrations tested. Neuregulin is the natural ligand for the HER2 receptor. (p-values as in FIG. 5).

Figure 5:
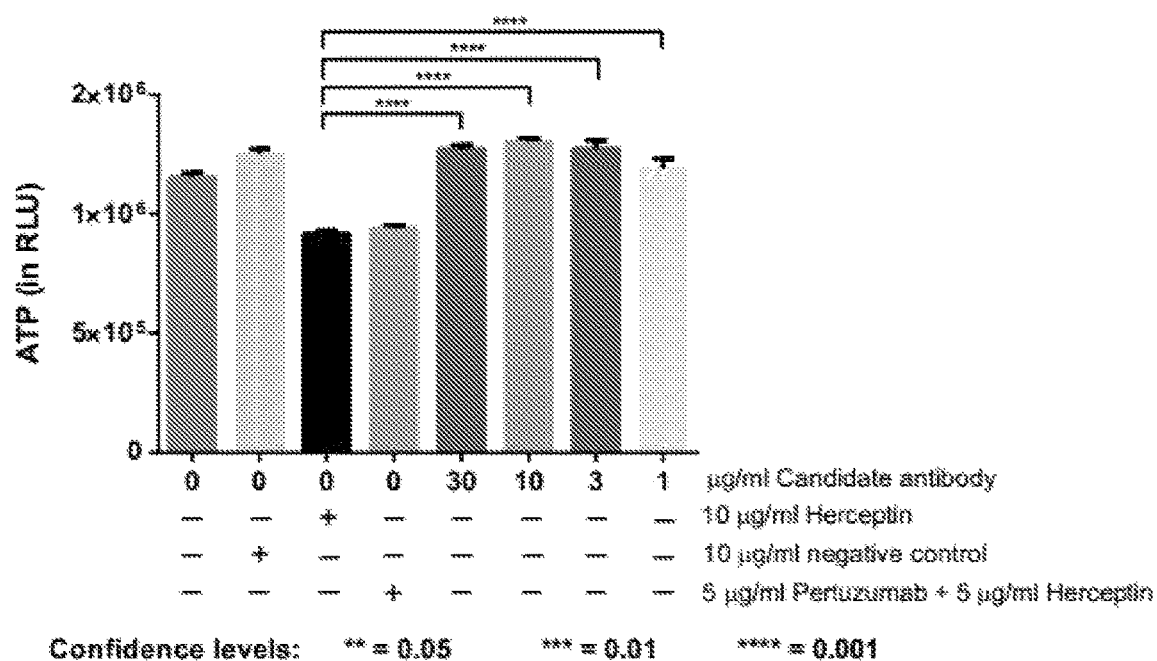
FIG. 5 shows that Herceptin toxicity can be detected in ATP assays depending on the glucose free fatty acid media in the presence of the mitochondrial toxicant doxorubicin, whereas no such effects were found for an alternative antibody against HER2.

FIG. 5 shows that herceptin toxicity can be detected in ATP assays depending on the glucose free fatty acid media in the presence of the mitochondrial toxicant doxorubicin, whereas no such effects were found for an alternative antibody against HER2./pct

The invention claimed is:

1. A method for predicting the cardiotoxicity of at least one test compound A, said method comprising:
   (a) culturing human stem-cell derived cardiomyocytes in a medium comprising fatty acids and carnitine and not comprising glucose and galactose;
   (b) treating the human stem-cell derived cardiomyocytes of step (a) with the at least one test compound A in the presence of a mitochondrial toxicant;
   (c) examining the human stem-cell derived cardiomyocytes for the cardiotoxic effect resulting from the treatment of step (b); and
   (d) comparing the results of step (c) with results obtained with control human stem-cell derived cardiomyocytes.

2. The method of claim 1, wherein the at least one test compound A is a receptor ligand for at least one receptor, or a modulator of a kinase, or a modulator of a phosphatase, or a modulator of an enzyme.

3. The method of claim 2, wherein said at least one test compound A is a receptor ligand for at least one receptor and said receptor is expressed by the human stem-cell derived cardiomyocytes.

4. The method of claim 1, wherein the at least one test compound A is an antibody.

5. The method of claim 2, wherein the human stem-cell derived cardiomyocytes are cultured in step (a) and/or treated in step (b) in the presence of a further receptor ligand for the at least one receptor, or a further modulator of the kinase, or a further modulator of the phosphatase, or a further modulator of the enzyme.

6. The method of claim 2, wherein the at least one test compound A is an agonist, partial agonist, antagonist, inverse agonist or an allosteric modulator of said at least one receptor or an inhibitor or stimulator of said kinase, phosphatase or enzyme.

7. The method of claim 1, wherein examining in step (c) is performed using an assay selected from the group consisting of an assay for determining ATP levels in the cardiomyocyte cells, assays for determining oxidative phosphorylation enzyme activity, assays for determining mitochondrial membrane potential, assay for determining basal respiration of the cardiomyocyte cells, assay to measure ATP turnover, assay to measure proton leak or assays to measure maximal respiration.

8. The method of claim 1, wherein the human stem-cell derived cardiomyocytes provided in step (a) are cultured in a medium comprising about 0.1 micromolar to 1 millimolar fatty acids and 0.5 mM (millimolar) to 3.5 mM of carnitine, but not comprising glucose and galactose.

9. The method of claim 1, wherein the human stem-cell derived cardiomyocytes that are provided in step (a) are obtained by proliferating human stem-cells in a first medium, followed by maturating the obtained cells in a second medium, followed by culturing the cells in a third medium, and wherein said third medium is a medium comprising fatty acids and carnitine and not comprising glucose and galactose.

10. The method of claim 1, wherein the human stem-cell derived cardiomyocytes provided in step (a) are cultured in said medium without glucose and galactose for a period of between 12-120 hours.

11. The method of claim 1, wherein the human stem-cell derived cardiomyocytes are treated in step (b) for a period of between 12-120 hours.

12. The method of claim 1, wherein the mitochondrial toxicant is selected from the group consisting of anthracyclines including doxorubicin, daunorubicin, epirubicin, idarubicin, valrubicin, and mitoxantrone, and combinations thereof.

13. The method of claim 2, wherein the at least one receptor is the human ERBB2 receptor.

14. The method of claim 5, wherein the further receptor ligand is Neuregulin.

15. The method of claim 1, wherein the mitochondrial toxicant is a cardiotoxic compound.

16. The method of claim 2, wherein said at least one test compound A is a receptor ligand for at least one receptor and said receptor is a cell surface receptor.

* * * * *